US012430853B2

(12) United States Patent
Miyamoto

(10) Patent No.: US 12,430,853 B2
(45) Date of Patent: Sep. 30, 2025

(54) IMAGE PROCESSING APPARATUS, IMAGE DISPLAY SYSTEM, IMAGE PROCESSING METHOD, AND PROGRAM

(71) Applicant: FUJIFILM Corporation, Tokyo (JP)

(72) Inventor: Masaki Miyamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 176 days.

(21) Appl. No.: 17/945,087

(22) Filed: Sep. 15, 2022

(65) Prior Publication Data

US 2023/0005222 A1    Jan. 5, 2023

Related U.S. Application Data

(63) Continuation of application No. PCT/JP2021/009727, filed on Mar. 11, 2021.

(30) Foreign Application Priority Data

Mar. 16, 2020 (JP) ................................ 2020-044961

(51) Int. Cl.
*G06T 19/00* (2011.01)
*A61B 6/46* (2024.01)

(52) U.S. Cl.
CPC .............. *G06T 19/00* (2013.01); *A61B 6/466* (2013.01); *G06T 2210/41* (2013.01); *G06T 2219/008* (2013.01)

(58) Field of Classification Search
CPC ................. G06T 19/00; G06T 2210/41; G06T 2219/008; G06T 11/008; G06T 19/003;
(Continued)

(56) References Cited

U.S. PATENT DOCUMENTS 5,371,778 A * 12/1994 Yanof ................. G06F 3/04845
378/4
8,331,635 B2 * 12/2012 Hilbelink .............. G06T 7/0012
382/128
(Continued)

FOREIGN PATENT DOCUMENTS

JP       2001101061          4/2001
JP       2001101061 A    *   4/2001
(Continued)

OTHER PUBLICATIONS

JP 2007289347A (Machine Translation on May 4, 2024) (Year: 2007).*

(Continued)

*Primary Examiner* — Michael Le
(74) *Attorney, Agent, or Firm* — JCIPRNET

(57) ABSTRACT

An image processing apparatus, an image display system, an image processing method, and a program by which it is possible to display an optimum three dimensional image when display is switched from a two dimensional tomographic image to a three dimensional image are provided. The processor (14) outputs a tomographic image display signal representing a two dimensional tomographic image included in a first tomographic image group based on first imaging data obtained by imaging a subject, extracts a second tomographic image group having a smaller interval between tomographic images than the first tomographic image group, on the basis of second imaging data acquired in imaging corresponding to the imaging for acquiring the first imaging data, if a display switching signal indicating switching from display of the two dimensional tomographic image to display of a three dimensional image is acquired, and outputs a three dimensional image display signal rep-
(Continued)

resenting a three dimensional image generated on the basis of the extracted second tomographic image group.

15 Claims, 7 Drawing Sheets

(58) Field of Classification Search
CPC ..... G06T 2219/02; A61B 6/466; A61B 5/055; G01T 1/161
See application file for complete search history.

(56) References Cited

U.S. PATENT DOCUMENTS

| | | | |
|---|---|---|---|
| 2005/0105678 A1* | 5/2005 | Nakashima | A61B 6/5223 378/4 |
| 2006/0085407 A1* | 4/2006 | Kaminaga | G16H 10/20 |
| 2006/0228012 A1 | 10/2006 | Masuzawa | |
| 2008/0101536 A1* | 5/2008 | Sendai | A61B 6/469 378/22 |
| 2008/0260226 A1* | 10/2008 | Moriya | G06F 18/22 382/128 |
| 2012/0287238 A1* | 11/2012 | Onishi | A61B 1/0005 348/45 |
| 2014/0037177 A1* | 2/2014 | Endo | G06T 11/00 382/131 |
| 2015/0260814 A1* | 9/2015 | Sakurai | G01R 33/4835 324/322 |
| 2015/0335303 A1* | 11/2015 | Chandelier | A61B 6/466 345/427 |
| 2018/0185113 A1* | 7/2018 | Gregerson | G06T 7/74 |
| 2019/0197741 A1* | 6/2019 | Nishii | G06T 19/00 |
| 2019/0200893 A1* | 7/2019 | Grouchy | A61B 5/0044 |
| 2019/0239926 A1* | 8/2019 | Pavlovskaia | A61B 17/1703 |

FOREIGN PATENT DOCUMENTS

| | | | |
|---|---|---|---|
| JP | 2004194869 | | 7/2004 |
| JP | 2004194869 A | * | 7/2004 |
| JP | 2004215961 | | 8/2004 |
| JP | 2004215961 A | * | 8/2004 |
| JP | 2006110185 | | 4/2006 |
| JP | 2006312026 | | 11/2006 |
| JP | 2007289347 | | 11/2007 |
| JP | 2007289347 A | * | 11/2007 |
| JP | 2016508242 | | 3/2016 |
| JP | 6583875 | | 10/2019 |

OTHER PUBLICATIONS

JP 2004215961A (Machine Translation on May 4, 2024) (Year: 2004).*
JP2004194869A (Machine Translation on May 4, 2024) (Year: 2004).*
JP2001101061A (Machine Translation on May 4, 2024) (Year: 2001).*
"International Search Report (Form PCT/ISA/210) of PCT/JP2021/009727," mailed on May 11, 2021, with English translation thereof, pp. 1-6.
"Written Opinion of the International Searching Authority (Form PCT/ISA/237)" of PCT/JP2021/009727, mailed on May 11, 2021, with English translation thereof, pp. 1-8.
"Notice of Reasons for Refusal of Japan Counterpart Application", issued on Dec. 15, 2023, with English translation thereof, p. 1-p. 6.

* cited by examiner

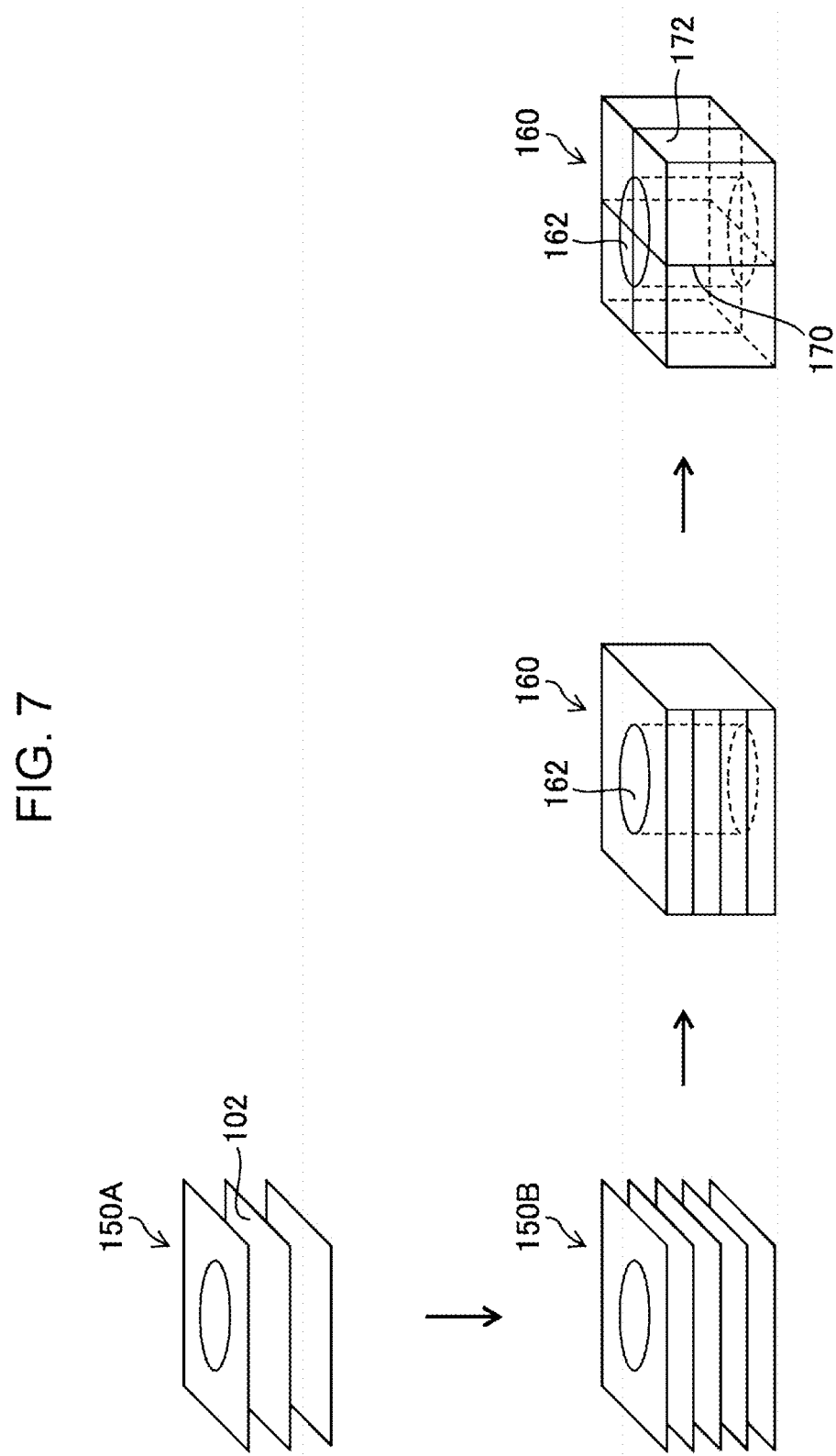

IMAGE PROCESSING APPARATUS, IMAGE DISPLAY SYSTEM, IMAGE PROCESSING METHOD, AND PROGRAM

CROSS-REFERENCE TO RELATED APPLICATIONS

The present application is a Continuation of PCT International Application No. PCT/JP2021/009727 filed on Mar. 11, 2021 claiming priority under 35 U.S.C § 119(a) to Japanese Patent Application No. 2020-044961 filed on Mar. 16, 2020. Each of the above applications is hereby expressly incorporated by reference, in its entirety, into the present application.

BACKGROUND OF THE INVENTION

1. Field of the Invention

The present invention relates to an image processing apparatus, an image display system, an image processing method, and a program.

2. Description of the Related Art

A multi-planar reconstruction method is known as three dimensional processing of projection data obtained by imaging a subject using a modality such as a CT imaging apparatus. The multi-planar reconstruction method can extract and display a given plane of three dimensionally constructed CT value information. For example, it is possible to switch display of an axial plane, which is a plane in the body axis direction, to display of a longitudinal, sagittal plane and display of a transverse, coronal plane. Note that CT is an abbreviation of Computed Tomography. The multi-planar reconstruction method is referred to as MPR using an abbreviation of Multi Planar Reconstruction.

JP2004-194869A describes an image display system including an image server and a display terminal, in which the image server and the display terminal are connected via a network. In the system described in JP2004-194869A, the display terminal receives a thick tomographic image group from the server, and displays a tomographic image from the received thick tomographic image group.

After receiving part of the thick tomographic image group, the system receives and stores a thin tomographic image group corresponding to the thick tomographic image group. Furthermore, when the thick tomographic image is displayed, upon an instruction for switching the display, the system switches the display of the thick tomographic image to the display of a thin tomographic image.

SUMMARY OF THE INVENTION

When a subject is imaged using a CT imaging apparatus, a thick slice image series in which an interval between tomographic images is about 5 millimeters and a thin slice image series in which an interval between tomographic images is about 1 millimeter may be reconstructed.

In image referencing for interpretation purposes, the thick slice image series is primarily applied. On the other hand, when the display is switched from an axial plane to a sagittal plane, an image series of the sagittal plane based on the thick slice image series is reconstructed. Then, the tomographic image of the sagittal plane is blurred in the body axis direction.

JP2004-194869A primarily discloses switching the axial plane, which is an original plane that is imaged, from a thick slice to a thin slice. JP2004-194869A also describes MPR, but does not specifically disclose MPR.

The present invention has been made in view of such circumstances, and an object thereof is to provide an image processing apparatus, an image display system, an image processing method, and a program by which it is possible to display an optimum three dimensional image when display is switched from a two dimensional tomographic image to a three dimensional image.

In order to achieve the above object, the following aspects of the invention are provided.

An image processing apparatus according to the present disclosure is an image processing apparatus including at least one processor configured to: output a tomographic image display signal representing a two dimensional tomographic image included in a first tomographic image group based on first imaging data obtained by imaging a subject; extract a second tomographic image group having a smaller interval between tomographic images than the first tomographic image group, on the basis of second imaging data acquired in imaging corresponding to the imaging for acquiring the first imaging data, if a display switching signal indicating switching from display of the two dimensional tomographic image to display of a three dimensional image is acquired; and output a three dimensional image display signal representing a three dimensional image generated on the basis of the extracted second tomographic image group. Here, the first imaging data and the second imaging data may be identical to each other.

According to the image processing apparatus according to the present disclosure, it is possible to display an optimal three dimensional image based on the second tomographic image group when switching from display of a two dimensional tomographic image to display of a three dimensional image.

The tomographic image may include a plane image having a thickness that is infinitely small.

Examples of the imaging data include raw data generated by an imaging apparatus that images a subject. An example of the raw data is projection data of a CT imaging apparatus.

In an image processing apparatus according to another aspect, the at least one processor is further configured to acquire the three dimensional image generated on the basis of the second tomographic image group.

According to this aspect, it is possible to display a three dimensional image using the three dimensional image generated in advance.

In an image processing apparatus according to another aspect, the at least one processor is further configured to extract the second tomographic image group having accessory information matching accessory information of the first tomographic image group.

According to this aspect, it is possible to extract the second tomographic image group using the accessory information of the first tomographic image group.

In an image processing apparatus according to another aspect, the at least one processor is further configured to extract the second tomographic image group on the basis of a degree of similarity between accessory information of the first tomographic image group and accessory information of the second tomographic image group.

According to this aspect, if there is no second tomographic image group having accessory information matching the accessory information of the first tomographic image group, it is possible to extract a second tomographic image group having accessory information similar to the accessory information of the first tomographic image group.

In an image processing apparatus according to another aspect, the at least one processor is further configured to extract the second tomographic image group using at least one of an imaging date and time, information representing content of a tomographic image group, or a position of a tomographic image in an imaging range of an imaging apparatus, as the accessory information.

According to this aspect, it is possible to extract the second tomographic image group using at least one of the imaging date and time of the first tomographic image group, the content of the tomographic image group, and the position of the tomographic image in the imaging range.

In an image processing apparatus according to another aspect, the at least one processor is further configured to set an interval between tomographic images included in the first tomographic image group.

According to this aspect, it is possible to define the interval between the tomographic images in the first tomographic image group.

In an image processing apparatus according to another aspect, the at least one processor is further configured to set an interval between tomographic images included in the second tomographic image group.

According to this aspect, it is possible to define the interval between the tomographic images in the second tomographic image group.

In an image processing apparatus according to another aspect, the processor extracts the second tomographic image group generated using the first imaging data from which the first tomographic image group is generated.

According to this aspect, it is possible to realize the display of the optimal three dimensional image generated on the basis of the imaging data serving as a basis of the first tomographic image group.

An image display system according to the present disclosure is an image display system including an image processing apparatus including at least one processor, and a display configured to display an image corresponding to an image display signal transmitted from the image processing apparatus. The at least one processor is configured to: output a tomographic image display signal representing a two dimensional tomographic image included in a first tomographic image group based on first imaging data obtained by imaging a subject; extract a second tomographic image group having a smaller interval between tomographic images than the first tomographic image group, on the basis of second imaging data acquired in imaging corresponding to the imaging for acquiring the first imaging data, if a display switching signal indicating switching from display of the two dimensional tomographic image to display of a three dimensional image is acquired; and output a three dimensional image display signal representing a three dimensional image generated on the basis of the extracted second tomographic image group. The display displays the three dimensional image corresponding to the output three dimensional image display signal.

An image processing method according to the present disclosure includes: outputting a tomographic image display signal representing a two dimensional tomographic image included in a first tomographic image group based on first imaging data obtained by imaging a subject; extracting a second tomographic image group having a smaller interval between tomographic images than the first tomographic image group, on the basis of second imaging data acquired in imaging corresponding to the imaging for acquiring the first imaging data, if a display switching signal indicating switching from display of the two dimensional tomographic image to display of a three dimensional image is acquired; and outputting a three dimensional image display signal representing a three dimensional image generated on the basis of the extracted second tomographic image group.

A program according to the present disclosure is a program for causing a computer to execute: outputting a tomographic image display signal representing a two dimensional tomographic image included in a first tomographic image group based on first imaging data obtained by imaging a subject; extracting a second tomographic image group having a smaller interval between tomographic images than the first tomographic image group, on the basis of second imaging data acquired in imaging corresponding to the imaging for acquiring the first imaging data, if a display switching signal indicating switching from display of the two dimensional tomographic image to display of a three dimensional image is acquired; and outputting a three dimensional image display signal representing a three dimensional image generated on the basis of the extracted second tomographic image group.

According to the present invention, it is possible to display an optimum three dimensional image based on a second tomographic image group when display is switched from a two dimensional tomographic image to a three dimensional image.

BRIEF DESCRIPTION OF THE DRAWINGS

FIG. 7 is an explanatory diagram of generation of a three dimensional image.

DESCRIPTION OF THE PREFERRED EMBODIMENTS

Figure 1:
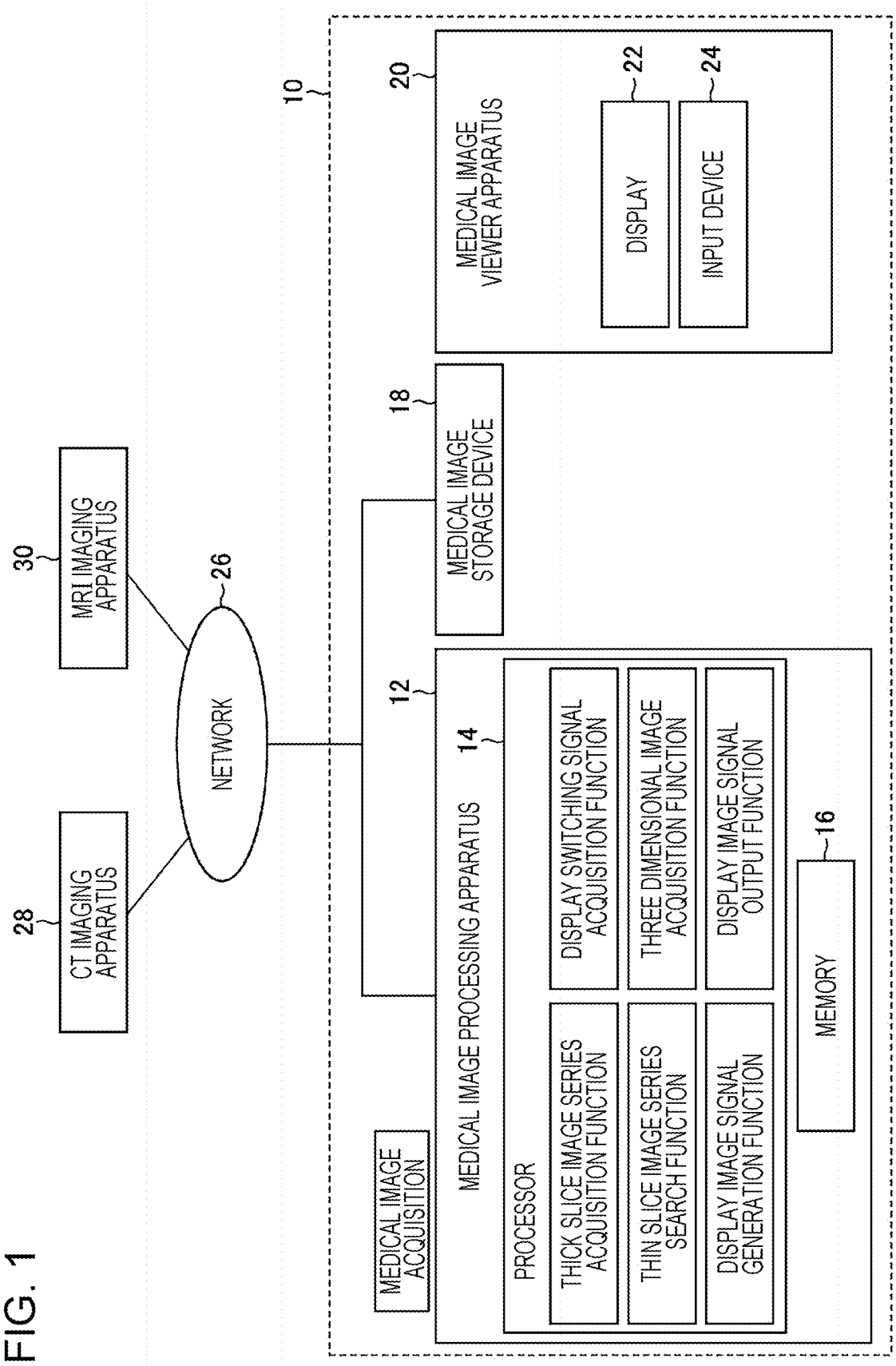
FIG. 1 is a functional block diagram of a medical image display system according to an embodiment.

Hereinafter, a preferred embodiment of the present invention will be described in detail with reference to the accompanying drawings. In the present specification, the same components are denoted by the same reference numerals, and overlapping description will be appropriately omitted.

Configuration Example of Medical Image Display System

Overall Configuration of Medical Image Display System

A medical image display system 10 searches for and extracts a thin slice image series corresponding to a thick slice image series when switching display of an axial plane to three dimensional display such as display of a sagittal plane during interpretation of a slice image of the axial plane. The medical image display system 10 acquires a three dimensional image reconstructed on the basis of the extracted thin slice image series, and displays the three dimensional image. Hereinafter, the medical image display system 10 will be described in detail.

Note that a slice interval applied to the thin slice image series is smaller than a slice interval applied to the thick slice image series. For example, the slice interval of the thin slice image series may be 1 millimeter, whereas the slice interval of the thick slice image series may be 5 millimeters. Note that the slice image refers to a tomographic image on a given plane. The tomographic image may include a plane image in which the thickness of a slice is infinitely small. The slice interval is synonymous with an interval between tomographic images.

The term "image" in this specification may be used to mean an image itself and image data representing an image. The image data is synonymous with an image signal representing an image.

Reconstruction refers to transformation and generation of image data acquired using a modality and image data derived from image data acquired using a modality. Examples of the reconstruction include generation of a slice image series including a plurality of slice images based on raw data and generation of a three dimensional image based on raw data.

Another example of the reconstruction is generation of a three dimensional image based on a slice image series. Examples of image processing for generating a three dimensional image include MIP (Maximum Intensity Projection), MPR, volume rendering, and the like. The raw data described in the embodiment is an example of imaging data.

FIG. 1 is a functional block diagram of the medical image display system according to the embodiment. The medical image display system 10 includes a medical image processing apparatus 12, a medical image storage device 18, and a medical image viewer apparatus 20.

The medical image processing apparatus 12 is a terminal apparatus used by a user in a hospital, an examination laboratory, or the like. A computer is applicable as the medical image processing apparatus 12. The medical image processing apparatus 12 includes a processor 14 and a memory 16. Note that the processor 14 described in the embodiment is an example of one or more processors.

The memory 16 may include a program memory in which programs including instructions to be executed by the processor 14 are stored. The memory 16 may include a data memory in which various types of data are stored.

The medical image processing apparatus 12 executes programs read out by the processor 14 from the memory 16 and implements various functions including a thick slice image series acquisition function, a display switching signal acquisition function, a thin slice image series search function, a three dimensional image acquisition function, a display image signal generation function, and a display image signal output function.

The thick slice image series acquisition may include a mode in which the processor 14 generates the thick slice image series from raw data or the like and acquires the generated thick slice image series.

The display switching signal acquisition function acquires a display switching signal or the like representing a display switching request input by a user or the like. The display image signal generation function generates a slice image display signal representing a slice image based on the thick slice image series and generates a three dimensional image display signal representing a three dimensional image based on the thin slice image series.

The display image signal output function outputs a slice image display signal and outputs a three dimensional image display signal. The slice image display signal described in the embodiment is an example of a tomographic image display signal.

The three dimensional image acquisition function may include a three dimensional image generation function. That is, if a desired three dimensional image is not stored in the medical image storage device 18, an original image, such as raw data, serving as a basis of the desired three dimensional image, can be acquired, and the desired three dimensional image can be generated from the original image.

The medical image storage device 18 stores medical images to which accessory information defined by the DICOM standard is added. Furthermore, patient information such as a patient name is given to the medical images. The patient information may be managed separately from the accessory information. The patient information may also be managed as the accessory information. The medical images stored using the medical image storage device 18 include a slice image series including a plurality of slice images.

The accessory information may include various kinds of information such as the date and time of an examination, a type of modality used for the examination, an examination item, and the number of images. The accessory information may include a series description for indicating the kind of image series to a user or the like. Details of the accessory information will be described later.

The medical images stored using the medical image storage device 18 may include raw data acquired using modalities such as a CT imaging apparatus 28 and an MM imaging apparatus 30 for imaging a subject, and reconstructed images such as three dimensional images reconstructed from the raw data. Details of the reconstructed image will be described later.

A large-capacity storage device is applicable as the medical image storage device 18. Note that DICOM is an abbreviation of Digital Imaging and Communication in Medicine.

The medical image viewer apparatus 20 is used when a user observes a medical image. The medical image viewer apparatus 20 includes a display 22 and an input device 24. The display 22 displays an image represented by a display image signal acquired from the medical image processing apparatus 12. The display 22 may display a medical image stored in the medical image storage device 18 on the basis of a command from the medical image processing apparatus 12.

The input device 24 transmits an input signal corresponding to a user operation to the medical image processing apparatus 12. An operating member such as a keyboard, a mouse, or a joystick is applicable as the input device 24. The display 22 and the input device 24 may be integrally configured by applying the display 22 of a touch panel type.

The medical image display system 10 is communicably connected to a modality such as the CT imaging apparatus 28 via a network 26. A Local Area Network (LAN) is applicable as the network 26. An in-house LAN in a hospital or the like is applicable as the network 26. The network 26 may include an external network of a hospital or the like.

The modality may include a PET apparatus, an ultrasound diagnostic apparatus, a CR apparatus, and the like. Note that PET is an abbreviation of Positron Emission Tomography. CR is an abbreviation of Computed Radiography.

Procedure of Medical Image Processing Method

Figure 2:
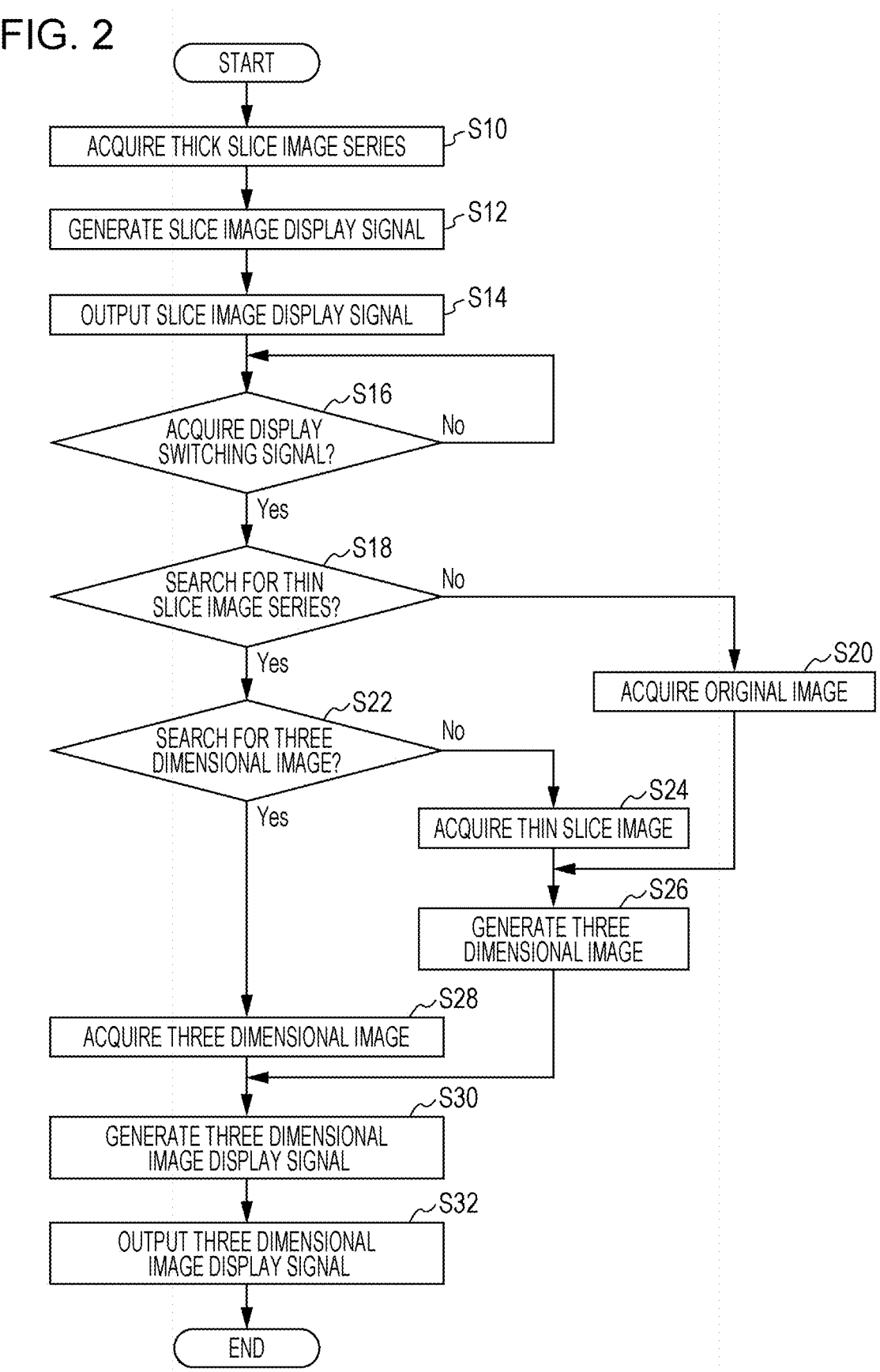
FIG. 2 is a flowchart illustrating a procedure of a medical image processing method according to the embodiment.

FIG. 2 is a flowchart illustrating a procedure of a medical image processing method according to the embodiment. In thick slice image series acquisition step S10, the processor 14 acquires a thick slice image series from the medical image storage device 18 or the like. After thick slice image series acquisition step S10, the process proceeds to slice image display signal generation step S12.

The thick slice image series includes a plurality of slice images. Note that the thick slice image series described in the embodiment is an example of a first tomographic image group. The slice image described in the embodiment is an example of a tomographic image.

In slice image display signal generation step S12, the processor 14 generates a slice image display signal for each of the slice images included in the acquired thick slice image series. After slice image display signal generation step S12, the process proceeds to slice image display signal output step S14.

In slice image display signal output step S14, the processor 14 outputs the slice image display signal generated in slice image display signal generation step S12. The display 22 which has received the slice image display signal displays the slice image.

As a display example of the slice image, there is a mode in which a slider bar indicating a position in the body axis direction is superimposed and displayed on a display screen on which a given slice image is displayed, and the slice image to be displayed on the display screen is switched depending on a moving operation of a slider. After slice image display signal output step S14, the process proceeds to display switching signal acquisition determination step S16.

In display switching signal acquisition determination step S16, the processor 14 determines whether or not a display switching signal is acquired. If the processor 14 determines in display switching signal acquisition determination step S16 that the display switching signal is not acquired, the determination is No. In a case of No determination, display switching signal acquisition determination step S16 is continued.

On the other hand, if the processor 14 determines in display switching signal acquisition determination step S16 that the display switching signal is acquired, the determination is Yes. In a case of Yes determination, the process proceeds to thin slice image series search step S18.

In thin slice image series search step S18, the processor 14 searches for a thin slice image series corresponding to the thick slice image series in which the slice image displayed on the display 22 is included. The search target is the medical image storage device 18 illustrated in FIG. 1. Note that the thin slice image series described in the embodiment is an example of a second tomographic image group.

If the processor 14 determines in thin slice image series search step S18 that the desired thin slice image series is not stored in the medical image storage device 18, the determination is No. In a case of No determination, the process proceeds to original image acquisition step S20.

In original image acquisition step S20, the processor 14 acquires an original image such as raw data and volume data used in generating the thick slice image series. If the original image is stored in the medical image storage device 18, the processor 14 acquires the original image from the medical image storage device 18.

If the original image is not stored in the medical image storage device 18, the medical image display system 10 searches an external storage device for the original image and acquires the original image. After original image acquisition step S20, the process proceeds to three dimensional image generation step S26.

In three dimensional image generation step S26, the processor 14 generates a three dimensional image from the original image. When a three dimensional image is generated from the original image in three dimensional image generation step S26, a thin slice image series may be generated from the original image, and a three dimensional image may be generated from the thin slice image series. After three dimensional image generation step S26, the process proceeds to three dimensional image display signal generation step S30.

On the other hand, if the processor 14 determines in thin slice image series search step S18 that the desired thin slice image series is stored in the medical image storage device 18, the determination is Yes. In a case of Yes determination, the process proceeds to three dimensional image search step S22.

In three dimensional image search step S22, the processor 14 determines whether or not a desired three dimensional image generated from the thin slice image series is stored in the medical image storage device 18. If the processor 14 determines in three dimensional image search step S22 that the desired three dimensional image is not stored in the medical image storage device 18, the determination is No. In a case of No determination, the process proceeds to thin slice image acquisition step S24.

In thin slice image acquisition step S24, the processor 14 acquires a thin slice image series stored in the medical image storage device 18. After thin slice image acquisition step S24, the process proceeds to three dimensional image generation step S26.

In three dimensional image generation step S26, the processor 14 generates the desired three dimensional image from the thin slice image series acquired in thin slice image acquisition step S24. After three dimensional image generation step S26, the process proceeds to three dimensional image display signal generation step S30.

On the other hand, if the processor 14 determines in three dimensional image search step S22 that the desired three dimensional image is stored in the medical image storage device 18, the determination is Yes. In a case of Yes determination, the process proceeds to three dimensional image acquisition step S28.

In three dimensional image acquisition step S28, the processor 14 acquires the desired three dimensional image from the medical image storage device 18. After three dimensional image acquisition step S28, the process proceeds to three dimensional image display signal generation step S30.

In three dimensional image display signal generation step S30, the processor 14 generates a three dimensional image display signal representing the desired three dimensional image. After three dimensional image display signal generation step S30, the process proceeds to three dimensional image display signal output step S32.

In three dimensional image display signal output step S32, the processor 14 outputs the three dimensional image display signal generated in three dimensional image display signal generation step S30. The display 22 which has received the three dimensional image display signal displays the three dimensional image.

Specific Examples of Slice Image Display and Three Dimensional Image Display

Next, specific examples of display switching from a slice image to a three dimensional image performed using the medical image display system 10 will be described.

Figure 3:
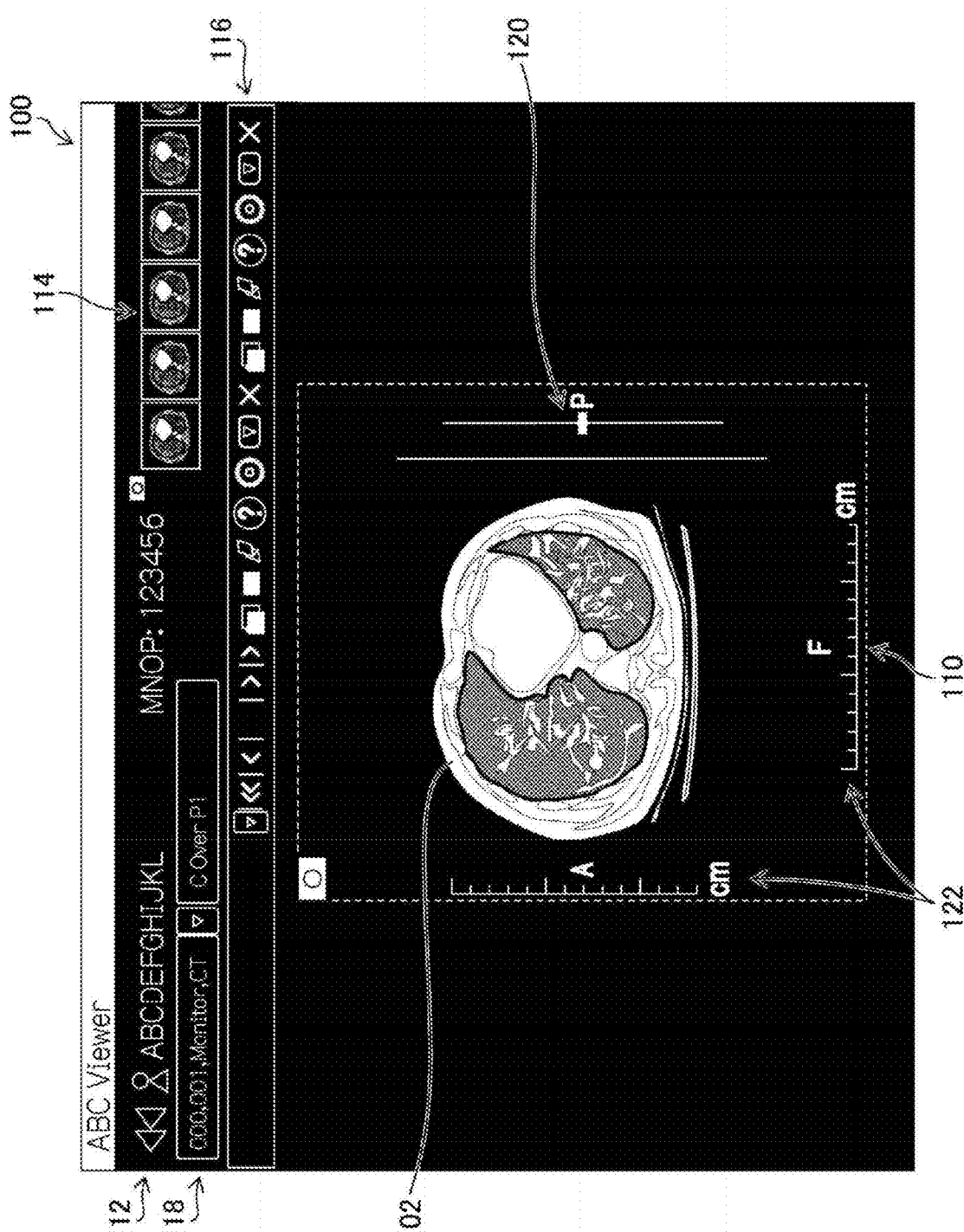
FIG. 3 is a schematic diagram of a display screen on which a slice image is displayed.

FIG. 3 is a schematic diagram of a display screen on which a slice image is displayed. A display screen 100 illustrated in FIG. 3 illustrates a slice image 102 of lungs obtained by imaging a subject using the CT imaging apparatus 28 illustrated in FIG. 1. The slice image 102 for interpretation is generated from a thick slice image series. Note that the slice image 102 described in the embodiment is an example of a two dimensional tomographic image.

The display screen 100 illustrated in FIG. 3 includes an image area 110, a patient information area 112, an examination list area 114, a tool bar 116, and status information 118. An observation target image is displayed in the image area 110. In the image area 110 illustrated in FIG. 3, the slice image 102, a slider bar 120, and a scale 122 are displayed.

If a user operates a slider, the slice image 102 corresponding to the position of the slider in the slider bar 120 is displayed. That is, a given slice image among the plurality of slice images is displayed in accordance with the operation of the slider by the user.

The patient information area 112 displays patient information about a patient, such as the patient's name, date of birth, age, and gender. The patient information may include information such as a patient ID. The examination list area 114 displays an examination list corresponding to the patient information displayed in the patient information area 112. In FIG. 3, thumbnails of medical images acquired in a plurality of examinations are displayed.

If a user selects a given thumbnail in the examination list, a medical image acquired in the selected examination is displayed in the image area 110. The display of the selected medical image may be full-screen display or reduced-screen display.

The tool bar 116 includes a plurality of buttons such as a display format switching button operated by a user to switch between display of the slice image and display of a three dimensional image. Each of the plurality of buttons corresponds to various functions on the display screen 100. If a user operates the display format switching button, the display of the slice image 102 is switched to the display of the three dimensional image corresponding to the slice image 102.

Examination information of the slice image 102, a name of a folder in which the slice image 102 is stored, a file name of the slice image 102, or the like is applicable as the status information 118. The examination information of the slice image 102 may include information such as the type of modality used for the examination, the date and time of the examination, and an examination institution.

Figure 4:
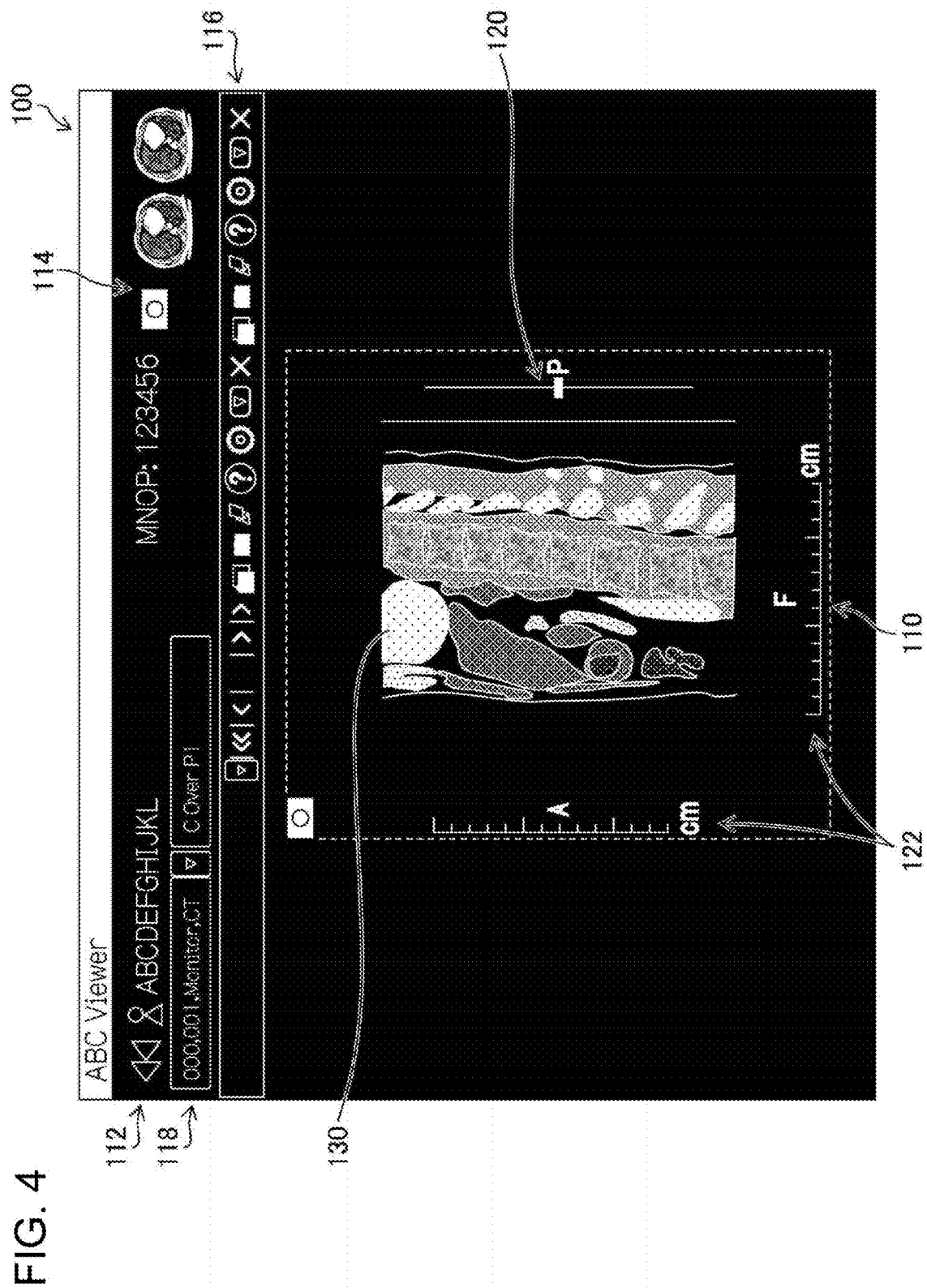
FIG. 4 is a schematic diagram of a display screen illustrating a display example of a three dimensional image.

FIG. 4 is a schematic diagram of a display screen illustrating a display example of a three dimensional image. As an example of a three dimensional image, a sagittal plane image 130 obtained by cutting out a plane in the sagittal direction is illustrated in FIG. 4. The sagittal plane image 130 is a three dimensional image based on a thin slice image series corresponding to the thick slice image series in which the slice image 102 is included.

That is, if a user observing the slice image 102 illustrated in FIG. 3 wants to see a sagittal plane of the slice image 102 and switches the display of the display screen 100, the sagittal plane image 130 illustrated in FIG. 4 is displayed.

Figure 5:
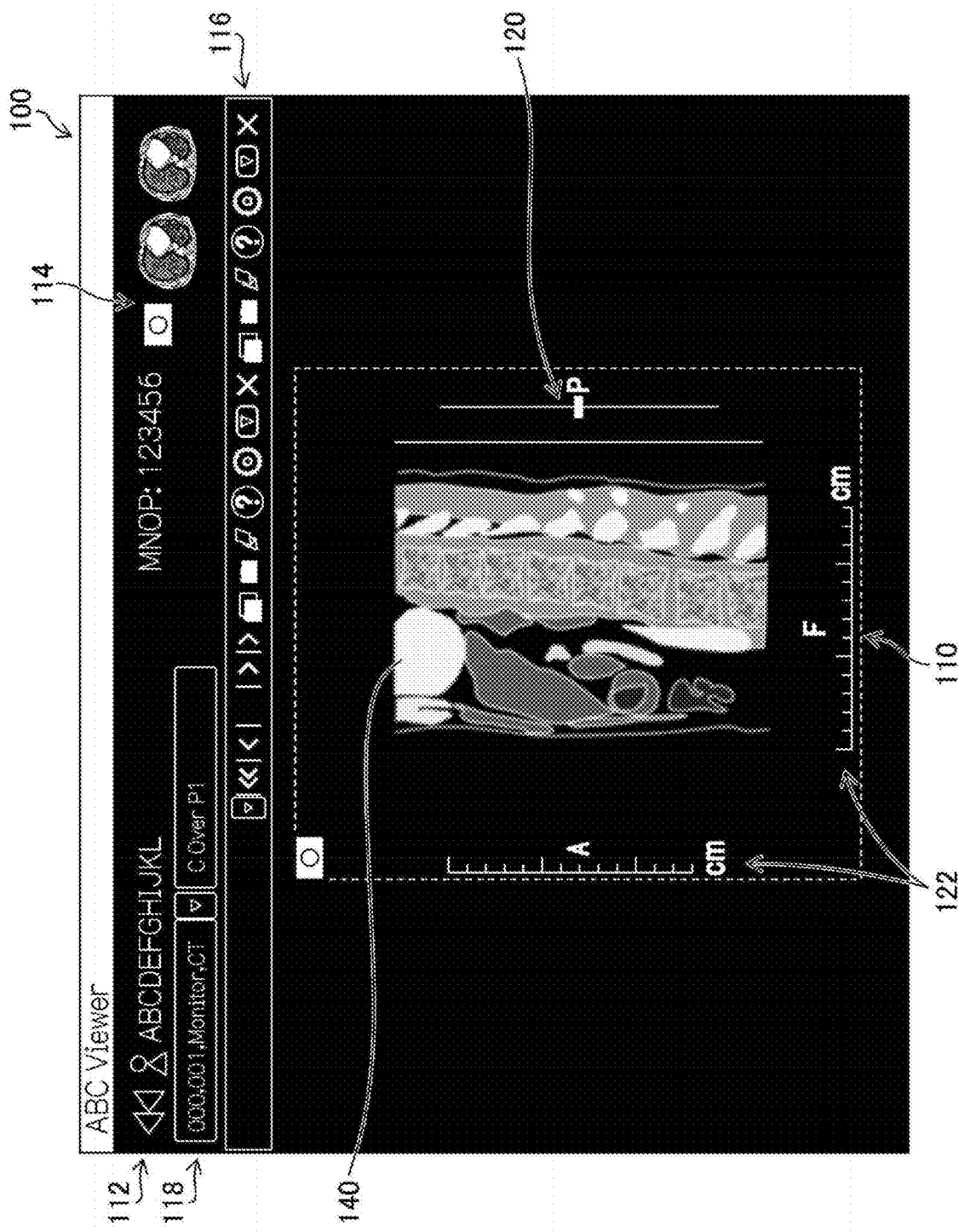
FIG. 5 is a schematic diagram of display of a sagittal plane according to a comparative example.

FIG. 5 is a schematic diagram of display of a sagittal plane according to a comparative example. A sagittal plane image 140 illustrated in FIG. 5 is generated using the thick slice image series in which the slice image 102 illustrated in FIG. 3 is included, and is blurred in the body axis direction.

This is because the interval between tomographic images of the thin slice image series is 1 millimeter, whereas the interval between tomographic images of the thick slice image series is 5 millimeters, and the blur in the body axis direction of the sagittal plane image 140 is caused by the resolution in the body axis direction.

The thick slice image series in which the slice image 102 illustrated in FIG. 3 is included may be generated as a thin slice image series from the same original image. Accordingly, a thin slice image series corresponding to the slice image 102 is searched for, and if the thin slice image series is present, the sagittal plane image 130 illustrated in FIG. 4 is generated using the thin slice image series.

Figure 6:
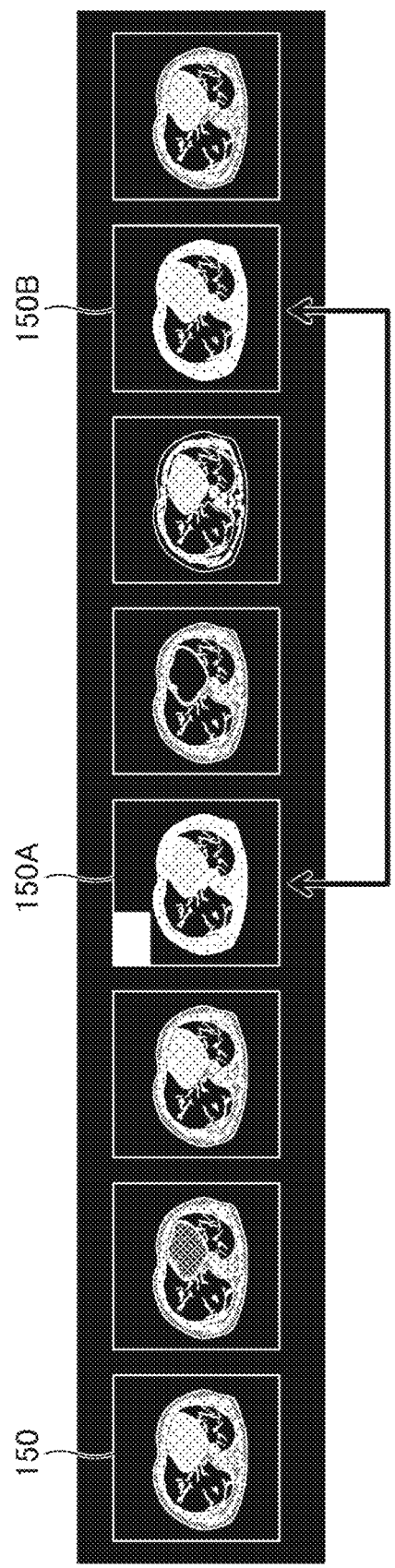
FIG. 6 is an explanatory diagram illustrating a correspondence relationship of a slice image series.

FIG. 6 is an explanatory diagram illustrating a correspondence relationship a slice image series. FIG. 6 illustrates a plurality of slice image series 150 detected using patient information. Upon acquiring a display switching signal, the processor 14 illustrated in FIG. 1 searches for and extracts a slice image series whose patient information matches the patient information of the slice image 102 displayed on the display screen 100 illustrated in FIG. 3, from the medical images stored in the medical image storage device 18 using the patient information as a parameter.

FIG. 6 illustrates an example in which a thin slice image series 150B corresponding to a thick slice image series 150A is automatically extracted.

FIG. 7 is an explanatory diagram of generation of a three dimensional image. The thin slice image series 150B corresponding to the thick slice image series 150A illustrated in FIG. 7 is extracted. The processor 14 generates volume data 160 on the basis of the thin slice image series 150B.

The processor 14 may generate the volume data 160 using the thin slice image series 150B, or may acquire raw data serving as a basis of the thin slice image series 150B and generate the volume data 160 of a subject 162 using the acquired raw data.

The processor 14 generates a sagittal plane image 170 using the volume data 160. The processor 14 may generate a three dimensional image, such as a coronal plane image 172, using the volume data 160.

Discrimination Between Thick Slice Image Series and Thin Slice Image Series

How many millimeters or less as the interval between tomographic images are handled as a thin slice image series is defined according to an imaging protocol for each examination facility. The processor 14 illustrated in FIG. 1 may have a slice image interval setting function of setting an interval between tomographic images of a thin slice image series. The setting of the interval between the tomographic images may include a mode of changing a predetermined initial value. The search for the thin slice image series may discriminate the thin slice image series on the basis of the set interval between the slice images.

Correspondence Relationship Between Thick Slice Image Series and Thin Slice Image Series Medical images acquired using the CT imaging apparatus 28 or the like are standardized by applying the DICOM standard. In the DICOM standard, an image is handled as a file. The file may include the image itself and accessory information of the image. The accessory information is information for a user or the like to know the kind of the image.

The accessory information of a thick slice image series can be used when searching for a thin slice image series. If the CT imaging apparatus 28 is applied to imaging of a subject, the thick slice image series and the thin slice image series can be generated from the same projection data. Accordingly, a thin slice image series having the same imaging date and time as a thick slice image series can be handled as a thin slice image series corresponding to the thick slice image series. Note that the projection data described in the embodiment is an example of imaging data.

Another example of the accessory information is a series description. The series description indicates the kind of an image series to a user or the like. The English notation Series Description may be used for the series description.

In search for the thin slice image series, a thin slice image series having the same series description as the thick slice image series can be handled as a thin slice image series corresponding to the thick slice image series.

If there is no thin slice image series whose series description completely matches that of the thick slice image series, a thin slice image series corresponding to the thick slice image series can be extracted on the basis of the degree of similarity of between the series descriptions of the two image series.

The series description may be divided into words, and the degree of similarity may be defined according to matching words. If the degree of similarity is a predetermined value or more, the series descriptions can be handled as similar series descriptions.

Another example of the accessory information is position information of each slice image in the modality. A two dimensional coordinate system defined on the imaging plane of the modality is applicable as the position information. That is, for the imaging range of the modality, the imaging range of each slice image is acquired using a minimum coordinate value and a maximum coordinate value of each slice image. A thin slice image series including slice images having the same imaging range or a similar imaging range can be handled as a thin slice image series corresponding to the thick slice image series.

In addition to the above-described imaging date and time, series description, and position information of the subject 162, various kinds of information can be defined as the accessory information. Such accessory information may be used to extract a thin slice image series corresponding to the thick slice image series.

A plurality of pieces of accessory information may be used to determine matching between the pieces of accessory information and the degree of similarity between the pieces of accessory information, and a thin slice image series corresponding to the thick slice image series may be extracted on the basis of the determination result. Note that the series description described in the embodiment is an example of information indicating content of a tomographic image group.

Advantageous Effects of Image Processing Apparatus, Image Display System, and Image Processing Method According to Embodiment The image processing apparatus, the image display system, and the image processing method according to the embodiment can obtain the following advantageous effects.

[1]
In the conventional display switching, it is necessary for a user to see thumbnails or the like displayed on a display screen to find a thin slice image series corresponding to a thick slice image series, perform an operation such as drag-and-drop to switch the thin slice image series used for screen display, and then switch to display of a three dimensional image such as the sagittal plane image 170 based on the thin slice image series.

In contrast, in the medical image display system 10 according to the present embodiment, if a display switching signal is acquired during the display of the slice image 102 based on the thick slice image series 150A, the processor 14 searches for the thin slice image series 150B corresponding to the thick slice image series 150A. The processor 14 generates the sagittal plane image 170 based on the thin slice image series 150B extracted as the search result. Thus, it is possible to realize the display of the sagittal plane image 170 or the like desired by the user, in which no blurring has occurred in the body axis direction, without the user being conscious of the thick slice image series or the thin slice image series.

[2]
The processor 14 performs a search using the accessory information of the thick slice image series 150A, and extracts the thin slice image series 150B corresponding to the thick slice image series 150A. Thus, it is possible to extract the thin slice image series 150B corresponding to the thick slice image series 150A based on the accessory information.

[3]
At least one of the imaging date and time, the series description, or the position information of an imaging target is applied as the accessory information. Thus, it is possible to extract the thin slice image series 150B corresponding to the thick slice image series 150A based on at least one of the imaging date and time, the series description, or the position information of the imaging target.

[4]
The processor 14 extracts the thin slice image series 150B having the accessory information similar to that of the thick slice image series 150A. Thus, it is possible to extract the thin slice image series 150B having similar accessory information even if there is no thin slice image series having completely matching accessory information.

Hardware Configuration of Processing Units and Control Unit

A hardware configuration of processing units that execute the processes of the medical image display system 10 and the medical image processing apparatus 12 described in the above embodiment is various processors. The various processors include a central processing unit (CPU), a programmable logic device (PLD), an application specific integrated circuit (ASIC), and the like.

The CPU is a general-purpose processor that executes programs and functions as various processing units. The PLD is a processor whose circuit configuration can be changed after manufacture. An example of the PLD is a field programmable gate array (FPGA). The ASIC is a dedicated electric circuit having a circuit configuration specifically designed to execute a specific process.

One processing unit may be configured by one of these various processors, or may be configured by two or more processors of the same type or different types. For example, one processing unit may be configured using a plurality of FPGAs or the like. One processing unit may be configured by combining one or more FPGAs and one or more CPUs.

In addition, a plurality of processing units may be configured using one processor. As an example of configuring a plurality of processing units using one processor, there is a form in which one processor is configured by combining one or more CPUs and software, and the one processor functions as a plurality of processing units. Such a form is represented by a computer such as a client terminal apparatus or a server apparatus.

As another configuration example, there is a form using a processor that implements the functions of the entire system including a plurality of processing units by using one IC chip. Such a form is represented by a system on chip or the like. Note that IC is an abbreviation of Integrated Circuit. A system on chip may also be referred to as an SoC using an abbreviation of system on chip.

In this manner, various processing units are constituted by one or more of the above various processors in terms of hardware configuration. More specifically, the hardware configuration of various processors is electric circuitry constituted by combining circuit elements such as semiconductor elements.

Example of Application to Program

It is possible to configure a program that causes a computer to implement various functions of the medical image display system 10 and the medical image processing apparatus 12 and each step of the image processing method described in the present specification. For example, it is possible to configure a program that causes a computer to implement processing corresponding to the thick slice image series acquisition function, the display switching signal acquisition function, the thin slice image series search function, the three dimensional image acquisition function, the display image signal generation function, and the display image signal output function illustrated in FIG. 4.

The display image signal output function described in the embodiment can include a three dimensional image display signal output function of outputting a three dimensional image display signal representing a three dimensional image generated on the basis of the second tomographic image group.

In the embodiment of the present invention described above, the constituent elements can be changed, added, or deleted as appropriate without departing from the gist of the present invention. The present invention is not limited to the embodiment described above, and various modifications can be made by a person having ordinary knowledge in the art within the technical thought of the present invention. In addition, the embodiment, the modifications, and the application example may be combined and implemented as appropriate.

Reference Signs List 10 medical image display system
12 medical image processing apparatus
14 processor
16 memory
18 medical image storage device
20 medical image viewer apparatus
22 display
24 input device
26 network
28 CT imaging apparatus
30 MRI imaging apparatus
100 display screen
102 slice image
110 image area
112 patient information area
114 examination list area
116 toolbar
118 status information
120 slider bar
122 scale
130 sagittal plane image
150 slice image series
150A thick slice image series
150B thin slice image series
160 volume data
162 subject
170 sagittal plane image
172 coronal plane image
S10 to S32 image processing method step

What is claimed is:

1. An image processing apparatus comprising
at least one processor configured to:
output a tomographic image display signal representing a two dimensional tomographic image showing a first plane perpendicular to a first imaging axis included in a first tomographic image group based on first imaging data obtained by imaging a subject;
when the two dimensional tomographic image included in the first tomographic image group is displayed, extract a second tomographic image group having a smaller interval between tomographic images in the first imaging axis than the first tomographic image group, on the basis of second imaging data acquired in imaging corresponding to the imaging for acquiring the first imaging data, if a display switching signal indicating switching from display of the two dimensional tomographic image to display of a three dimensional image showing a second plane intersecting the first plane is acquired,
wherein the processor is further configured to use accessory information of the two dimensional tomographic image displayed in a display screen for extracting the second tomographic image group that is corresponding to the first tomographic image group in which the two dimensional tomographic image displayed is included;
wherein the second plane is generated using the extracted second tomographic image group which has accessory information matching the accessory information of the two dimensional tomographic image displayed in the display screen and included in the first tomographic image group; and
output a three dimensional image display signal representing a three dimensional image showing the second plane generated using the extracted second tomographic image group.

2. The image processing apparatus according to claim 1, wherein the at least one processor is further configured to acquire the three dimensional image generated on the basis of the second tomographic image group.

3. The image processing apparatus according to claim 1, wherein the at least one processor is further configured to extract the second tomographic image group on the basis of a degree of similarity between the accessory information of the first tomographic image group and the accessory information of the second tomographic image group.

4. The image processing apparatus according to claim 3, wherein the at least one processor is further configured to:
apply a series description of the first tomographic image group as the accessory information of the first tomographic image group;
apply a series description of the second tomographic image group as the accessory information of the second tomographic image group;

divide the series description of the first tomographic image group into words, and divide the series description of the second tomographic image group into words; and define the degree of similarity according to matching between the words included in the series description of the first tomographic image group and the words included in the series description of the second tomographic image group.

5. The image processing apparatus according to claim 1, wherein the at least one processor is further configured to extract the second tomographic image group using at least one of an imaging date and time, information representing content of a tomographic image group, or a position of a tomographic image in an imaging range of an imaging apparatus, as the accessory information.

6. The image processing apparatus according to claim 1, wherein the at least one processor is further configured to set an interval between tomographic images included in the first tomographic image group.

7. The image processing apparatus according to claim 1, wherein the at least one processor is further configured to set an interval between tomographic images included in the second tomographic image group.

8. The image processing apparatus according to claim 1, wherein the at least one processor is further configured to extract the second tomographic image group generated using the first imaging data from which the first tomographic image group is generated.

9. The image processing apparatus according to claim 1, wherein the at least one processor is further configured to:
determine whether or not the second tomographic image group corresponding to the first tomographic image group is stored;
acquire a three dimensional image on which the first tomographic image group is based, in a case where it is determined that the second tomographic image group corresponding to the first tomographic image group is not stored; and
generate the second tomographic image group from the acquired three dimensional image.

10. The image processing apparatus according to claim 1, wherein the first plane is an axial plane, and the second plane is either a sagittal or coronal plane.

11. The image processing apparatus according to claim 1, wherein volume data is generated from the second tomographic image group, and the three dimensional image showing the second plane is generated from the volume data.

12. The image processing apparatus according to claim 1, wherein the second tomographic image group is automatically extracted having tomographic images having a same imaging range or a similar imaging range corresponding to the thick slice image series.

13. An image display system comprising:
an image processing apparatus comprising at least one processor; and
a display configured to display an image corresponding to an image display signal transmitted from the image processing apparatus, wherein
the at least one processor is configured to:
output a tomographic image display signal representing a two dimensional tomographic image showing a first plane perpendicular to a first imaging axis included in a first tomographic image group based on first imaging data obtained by imaging a subject;
when the two dimensional tomographic image included in the first tomographic image group is displayed, extract a second tomographic image group having a smaller interval between tomographic images in the first imaging axis than the first tomographic image group, on the basis of second imaging data acquired in imaging corresponding to the imaging for acquiring the first imaging data, if a display switching signal indicating switching from display of the two dimensional tomographic image to display of a three dimensional image showing a second plane intersecting the first plane is acquired,
wherein the processor is further configured to use accessory information of the two dimensional tomographic image displayed in a display screen for extracting the second tomographic image group that is corresponding to the first tomographic image group in which the two dimensional tomographic image displayed is included;
wherein the second plane is generated using the extracted second tomographic image group which has accessory information matching the accessory information of the two dimensional tomographic image displayed in the display screen and included in the first tomographic image group; and
output a three dimensional image display signal representing a three dimensional image showing the second plane generated using the extracted second tomographic image group, and
the display displays the three dimensional image corresponding to the output three dimensional image display signal.

14. An operation method of an image processing apparatus, comprising:
outputting, by a computer, a tomographic image display signal representing a two dimensional tomographic image showing a first plane perpendicular to a first imaging axis included in a first tomographic image group based on first imaging data obtained by imaging a subject;
when the two dimensional tomographic image included in the first tomographic image group is displayed, extracting, by a computer, a second tomographic image group having a smaller interval between tomographic images in the first imaging axis than the first tomographic image group, on the basis of second imaging data acquired in imaging corresponding to the imaging for acquiring the first imaging data, if a display switching signal indicating switching from display of the two dimensional tomographic image to display of a three dimensional image showing a second plane intersecting the first plane is acquired,
using accessory information of the two dimensional tomographic image displayed in a display screen for extracting the second tomographic image group that is corresponding to the first tomographic image group in which the two dimensional tomographic image displayed is included
wherein the second plane is generated using the extracted second tomographic image group which has accessory information matching the accessory information of the two dimensional tomographic image displayed in the display screen and included in the first tomographic image group; and
outputting, by a computer, a three dimensional image display signal representing a three dimensional image showing the second plane generated using the extracted second tomographic image group.

15. A non-transitory, computer-readable tangible recording medium which records thereon a program for causing, when read by a computer, the computer to perform the operation method of an image processing apparatus according to claim 12.

\* \* \* \* \*